United States Patent
Sathaye et al.

(10) Patent No.: US 9,295,845 B2
(45) Date of Patent: Mar. 29, 2016

(54) POST-MI PACING WITH AUTOCAPTURE FUNCTION

(75) Inventors: Alok S. Sathaye, Minneapolis, MN (US); Joseph M. Pastore, Woodbury, MN (US); Scott A. Meyer, Rochester, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2289 days.

(21) Appl. No.: 11/427,517

(22) Filed: Jun. 29, 2006

(65) Prior Publication Data

US 2008/0004669 A1   Jan. 3, 2008

(51) Int. Cl.
*A61N 1/00* (2006.01)
*A61N 1/362* (2006.01)
*A61N 1/37* (2006.01)

(52) U.S. Cl.
CPC ............ *A61N 1/3627* (2013.01); *A61N 1/3712* (2013.01); *A61N 1/37* (2013.01); *A61N 1/371* (2013.01)

(58) Field of Classification Search
CPC ............ A61N 1/00; A61N 1/02; A61N 1/04; A61N 1/05; A61N 1/08; A61N 1/18; A61N 1/362; A61N 1/365; A61N 1/368; A61N 1/37; A61N 1/371
USPC ................................................. 128/897–899
See application file for complete search history.

(56) References Cited

U.S. PATENT DOCUMENTS

| 5,935,160 | A | 8/1999 | Auricchio et al. | |
|---|---|---|---|---|
| 6,128,535 | A * | 10/2000 | Maarse | 607/28 |
| 6,615,089 | B1 | 9/2003 | Russie et al. | |
| 6,628,988 | B2 * | 9/2003 | Kramer et al. | 607/9 |
| 6,643,546 | B2 * | 11/2003 | Mathis et al. | 607/9 |
| 6,865,420 | B1 | 3/2005 | Kroll | |
| 6,915,160 | B2 | 7/2005 | Auricchio et al. | |
| 6,937,901 | B2 * | 8/2005 | Zhu et al. | 607/27 |
| 6,965,797 | B2 | 11/2005 | Pastore et al. | |
| 6,973,349 | B2 | 12/2005 | Salo | |
| 7,295,874 | B2 * | 11/2007 | Prinzen et al. | 607/9 |
| 2002/0161410 | A1 | 10/2002 | Kramer et al. | |
| 2003/0105493 | A1 | 6/2003 | Salo | |
| 2004/0030357 | A1 | 2/2004 | Salo et al. | |
| 2004/0049236 | A1 | 3/2004 | Kramer et al. | |
| 2007/0055317 | A1 * | 3/2007 | Stahmann et al. | 607/23 |

* cited by examiner

*Primary Examiner* — Eric D. Bertram
*Assistant Examiner* — Elizabeth K So
(74) *Attorney, Agent, or Firm* — Schwegman Lundberg & Woessner, P.A.

(57) ABSTRACT

A method and apparatus is described for preventing or reducing the ventricular remodeling that normally occurs after a myocardial infarction using pacing therapy. By pacing sites in proximity to the infarct with appropriately timed pacing pulses, the infarct region is pre-excited in a manner that lessens the mechanical stress to which it is subjected, thus reducing the stimulus for remodeling. If capture by the pacing pulses is not being achieved, the device may be configured to change the pacing pulse energy and/or pacing site as appropriate.

9 Claims, 4 Drawing Sheets

POST-MI PACING WITH AUTOCAPTURE FUNCTION

RELATED CASES

This application is related to U.S. Pat. Nos. 6,628,988, 6,973,349, 6,915,160 and 6,965,797 which are hereby incorporated by reference in their entirety.

FIELD OF THE INVENTION

This invention pertains to cardiac rhythm management devices such as pacemakers and other implantable devices.

BACKGROUND

A myocardial infarction is the irreversible damage done to a segment of heart muscle by ischemia, where the myocardium is deprived of adequate oxygen and metabolite removal due to an interruption in blood supply. It is usually due to a sudden thrombotic occlusion of a coronary artery, commonly called a heart attack. If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm where all of the muscle fibers in the area are destroyed and replaced by fibrous scar tissue.

Even if the ventricular dysfunction as a result of the infarct is not immediately life-threatening, a common sequela of a transmural myocardial infarction, especially in the left ventricle, is heart failure brought about by ventricular remodeling. Ventricular remodeling is a physiological process in response to the hemodynamic effects of the infarct that causes changes in the shape and size of the ventricle. Remodeling is initiated in response to a redistribution of cardiac stress and strain caused by the impairment of contractile function in the infarcted area as well as in nearby and/or interspersed viable myocardial tissue with lessened contractility due to the infarct. Following a transmural infarction, the infarcted area includes tissue undergoing ischemic necrosis and is surrounded by normal myocardium. Until scar tissue forms, the area around the infarcted area is particularly vulnerable to the distending forces within the ventricle and undergoes expansion over a period of hours to days. Over the next few days and months after scar tissue has formed, global remodeling and chamber enlargement occur due to complex alterations in the architecture of the ventricle involving both infarcted and non-infarcted areas.

Remodeling is thought to be the result of a complex interplay of hemodynamic, neural, and hormonal factors that occur primarily in response to myocardial wall stress. One physiological compensatory mechanism that acts to increase cardiac output is increased diastolic filling pressure of the ventricles as an increased volume of blood is left in the lungs and venous system. This increases the preload, which is the degree to which the ventricles are stretched by the volume of blood in the ventricles at the end of diastole. An increase in preload causes an increase in stroke volume during systole, a phenomena known as the Frank-Starling principle. The ventricular dilation resulting from the increased preload causes increased ventricular wall stress at a given systolic pressure in accordance with Laplace's law. Along with the increased pressure-volume work done by the ventricle, this acts as a stimulus for compensatory hypertrophy of the ventricular myocardium. Hypertrophy can increase systolic pressures but, if the hypertrophy is not sufficient to meet the increased wall stress, further and progressive dilation results. This non-compensatory dilation causes wall thinning and further impairment in left ventricular function. It also has been shown that the sustained stresses causing hypertrophy may induce apoptosis (i.e., programmed cell death) of cardiac muscle cells. Thus, although ventricular dilation and hypertrophy may at first be compensatory and increase cardiac output, the process ultimately results in further deterioration and dysfunction. It has been found that the extent of left ventricular remodeling in the late period after an infarction, as represented by measurements of end-systolic and end-diastolic left ventricular volumes, is an even more powerful predictor of subsequent mortality than the extent of coronary artery disease.

SUMMARY

Described herein is a method and apparatus for preventing or reducing the ventricular remodeling that normally occurs after a myocardial infarction using pacing therapy. The part of the myocardium that is most vulnerable to the post-infarct remodeling process is the infarct region, which is an area that includes sites in and around the infarct where the myocardial fibers are still intact but contractile function is impaired. The infarct region is thus the area most likely to undergo the progressive non-compensatory dilation described above with wall thinning and further impairment of function. By pacing sites in proximity to the infarct with appropriately timed pacing pulses, the infarct region is pre-excited in a manner that lessens the mechanical stress to which it is subjected, thus reducing the stimulus for remodeling. Because pre-excitation of a myocardial site to reduce stress is only effective if the pacing pulse captures the site, the device may also be configured to determine if capture by pre-excitation is being achieved through detection of an evoked response at the site. If capture is not being achieved, the device may then be further configured to change the pacing pulse energy and/or pacing site as appropriate.

DETAILED DESCRIPTION

Figure 1:
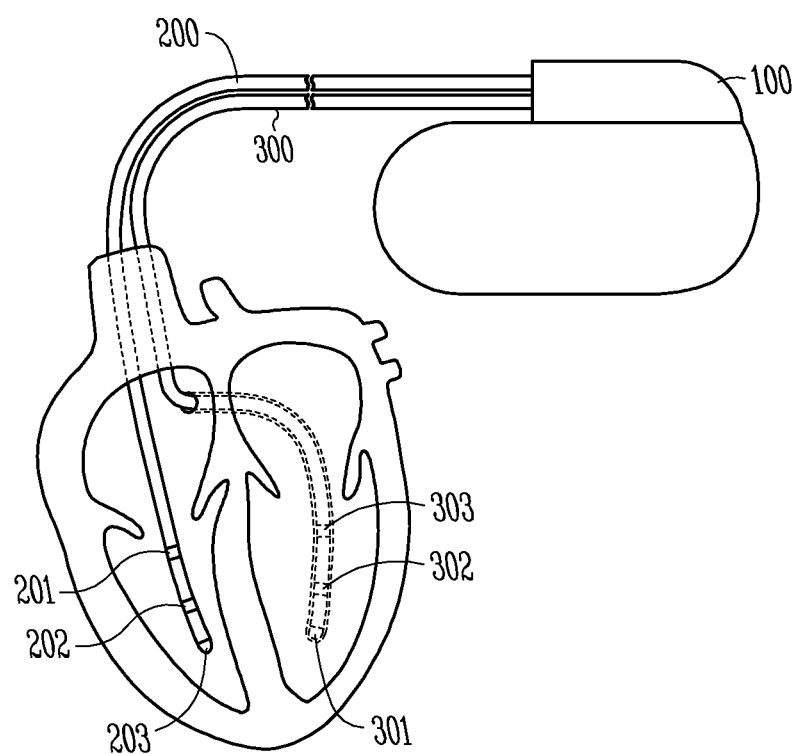
FIG. 1 illustrates the physical configuration of an exemplary pacing device.

The degree to which a heart muscle fiber is stretched before it contracts is termed the preload, while the degree of tension or stress on a heart muscle fiber as it contracts is termed the afterload. The maximum tension and velocity of shortening of a muscle fiber increases with increasing preload. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Thus, if a ventricular region can be made to contract earlier than parts of the ventricle, it will be subjected to both a decreased preload and afterload which decreases the mechanical stress experienced by the region relative to other regions during systolic contraction. The region will also do less work thus lessening its metabolic demands and the degree of any ischemia that may be present.

If the region around an infarct were made to contract during early systole, it would be subjected to less distending forces and less likely to undergo expansion, especially during the period immediately after a myocardial infarction. In order to cause early contraction and lessened stress, electro-stimulatory pacing pulses may be delivered to one or more sites in or around the infarct in a manner that pre-excites those sites relative to the rest of the ventricle. (As the term is used herein, a pacing pulse is any electrical stimulation of the heart of sufficient energy to initiate a propagating depolarization, whether or not intended to enforce a particular heart rate.) In a normal heartbeat, the specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode. Pre-excitation of a paced site relative to other sites can be used to deliberately change the distribution of wall stress experienced by the ventricle during the cardiac pumping cycle in order to prevent or reduce the remodeling that would otherwise occur. This deliberate change in the distribution of wall stress by pre-excitation pacing will mechanically unload the overstressed region of the ventricular myocardium. Pre-excitation of the infarct region relative to other regions unloads the infarct region from mechanical stress by decreasing its afterload and preload, thus preventing or minimizing the remodeling that would otherwise occur. Pacing therapy to unload the infarct region may be implemented by pacing the ventricles at a single site in proximity to the infarct region or by pacing at multiple ventricular sites in such proximity. In the latter case, the pacing pulses may be delivered to the multiple sites simultaneously or in a defined pulse output sequence. The single-site or multiple site pacing may be performed in accordance with a bradycardia pacing algorithm such as an inhibited demand mode or a triggered mode.

FIG. 1 shows an implantable cardiac device 100 for delivering pre-excitation therapy to an infarct region as well as possibly other types of pacing therapy. Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device may sense intrinsic cardiac electrical activity through a sensing channel which incorporates one or more of the electrodes. In order to excite myocardial tissue in the absence of an intrinsic beat, a pacing pulse with energy above a certain threshold is delivered to the pacing site through a pacing channel which incorporates one or more of the electrodes.

In an exemplary embodiment, the implantable device for delivering therapy to post-MI patients includes one or more pacing channels for delivering pacing pulses to one or more ventricular sites. The controller is programmed to deliver pacing which pre-excites a region of the ventricular myocardium in the vicinity of the infarct so as to mechanically unload that region during systole. The therapy may be delivered as single-site pacing, biventricular pacing where one of the ventricles is pre-excited relative to the other as determined by a programmed biventricular offset interval, or delivered as multi-site ventricular pacing where at least one of the ventricles is paced at a plurality of sites so as to pre-excite one or more of the sites relative to the other sites. In the case where the pre-excitation pacing is delivered at multiple sites, the sites may be paced simultaneously or in accordance with a particular pulse output sequence that specifies the order in which the sites are to be paced during a single beat. Pre-excitation pacing of one or more ventricular sites in proximity to an infarct may be delivered in conjunction with a bradycardia pacing mode, which refers to a pacing algorithm that enforces a certain minimum heart rate, and may include or not include pacing pulses delivered to the atria or ventricles for other purposes (e.g., treatment of bradycardia). Inhibited demand bradycardia pacing modes utilize escape intervals to control pacing in accordance with sensed intrinsic activity. In an inhibited demand ventricular pacing mode, the ventricle is paced during a cardiac cycle only after expiration of a defined escape interval during which no intrinsic beat by the chamber is detected. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL). In atrial tracking and AV sequential pacing modes, another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before the expiration. Because it is only paced beats that pre-excite the infarct region, it may be desirable in certain patients to decrease the AVI to be below the intrinsic PR interval (i.e., the normal time for an intrinsic ventricular beat to occur after an atrial sense or pace) or increase the LRL to be slightly above the patient's normal resting heart rate.

In order to pre-excite an infarct region, one or more pacing electrodes must be placed in proximity to the region. The area of the infarct can be identified by a number of means, including ultrasonic imaging, PET scans, thallium scans, and MRI perfusion scans. In the case of a left ventricular infarct, epicardial leads can either be placed directly on the epicardium with a thoracotomy (an open chest surgical operation) or a thoracoscopic procedure, or leads can be threaded from the upper venous system into a cardiac vein via the coronary sinus. (See, e.g., U.S. Pat. No. 5,935,160 issued to Auricchio et al., and assigned to Cardiac Pacemakers, Inc., which is hereby incorporated by reference.) In one embodiment, the device utilizes one or more multi-electrode leads each having a plurality of electrodes in order to excite different myocardial sites. FIG. 1 shows the exemplary device having two leads 200 and 300, each of which is a multi-electrode lead having electrodes 201-203 and 301-303, respectively. The electrodes 201-203 are disposed in the right ventricle in order to excite right ventricular or septal regions, while the electrodes 301-303 are disposed in the coronary sinus in order to excite regions of the left ventricle. Other embodiments may use a plurality of single-electrode leads in order to excite different pacing sites. As explained below, once the device and leads are implanted, the pacing and/or sensing channels of the device may be configured with selected ones of the multiple electrodes in order to selectively pace or sense a particular myocardial site.

A block diagram of an exemplary device for delivering pre-excitation pacing therapy to a site or sites in proximity to an infarct as described above is illustrated in FIG. 2. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The functions performed by the device as described herein should be understood to be performed by the controller and/or other dedicated circuitry. The controller controls the overall operation of the device in accordance with programmed instructions stored in memory. The controller interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or sensing channel exceeds a specified threshold, the controller detects an atrial or ventricular sense, respectively, which pacing algorithms may employ to trigger or inhibit pacing. The controller is capable of operating the device in a number of programmed modes where a programmed mode defines how pacing pulses are output in response to sensed events and expiration of time intervals. A telemetry interface 80 is also provided for communicating with an external programmer and by which the programming of the controller and device configuration may be modified.

Figure 2:
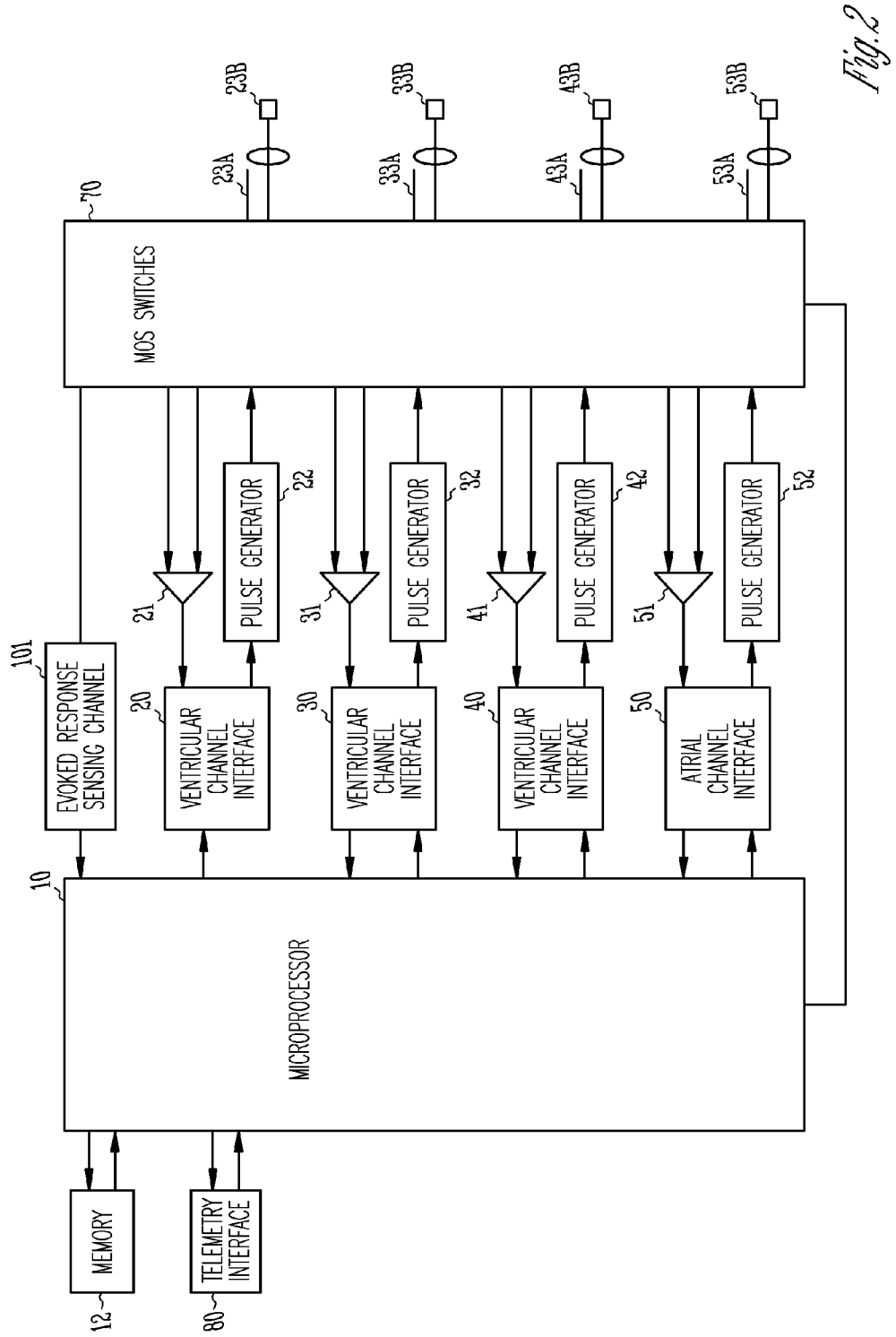
FIG. 2 is a block diagram of an exemplary pacing device.

The device illustrated in FIG. 2 has multiple sensing and pacing channels and is therefore capable of delivering single-site or multiple site ventricular pre-excitation pacing for purposes of stress reduction as well as conventional pacing. The multiple sensing and pacing channels may be configured as either atrial or ventricular channels. The device may have any number of configurable sensing or pacing channels, but shown in FIG. 2 for purposes of example is a configuration with one atrial sensing/pacing channel and three ventricular sensing/pacing channels. The atrial sensing/pacing channel comprises ring electrode 53*a*, tip electrode 53*b*, sense amplifier 51, pulse generator 52, and an atrial channel interface 50 which communicates bi-directionally with a port of microprocessor 10. The three ventricular sensing/pacing channels include ring electrodes 23*a*, 33*a*, and 43*a*, tip electrodes 23*b*, 33*b*, and 43*b*, sense amplifiers 21, 31, and 41, pulse generators 22, 32, and 42, and ventricular channel interfaces 20, 30, and 40. The channel interfaces include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A pacing channel is made up of a pulse generator connected to an electrode while a sensing channel is made up of a sense amplifier connected to an electrode. The device may be equipped with any number of pulse generators, amplifiers, and electrodes than may be combined arbitrarily to form sensing or pacing channels. In the illustrated embodiment, bipolar leads that include ring and tip electrodes are used for outputting a pacing pulse and/or sensing intrinsic activity. Other embodiments may employ a single electrode referenced to the device housing or an indifferent electrode for a sensing or pacing channel, known as a unipolar lead. Multiple electrodes may also be incorporated into a single lead.

A MOS switch matrix 70 controlled by the microprocessor is used to switch selected electrodes to the input of a sense amplifier or to the output of a pulse generator in order to configure a sensing or pacing channel, respectively. The switch matrix 70 also allows selected ones of the available implanted electrodes to be incorporated into a sensing or pacing channel. Of particular relevance to the present discussion, the switch matrix also allows particular myocardial sites to be pre-excited for purposes of stress reduction by selecting the appropriate electrode(s) to be incorporated into a pacing channel used to deliver pre-excitation pacing. Configuration of pacing and sensing channels may be performed via an external programmer communicating through the telemetry interface or, as discussed below, may be performed automatically by the microprocessor executing a configuration algorithm.

As noted above, the device allows adjustment of the pacing pulse energy in order to ensure capture of myocardial tissue (i.e., initiating of a propagating action potential) by a pacing pulse. Myocardial sites in proximity to an infarct or within ischemic regions may be less excitable than normal and require an increased pacing energy in order to achieve capture. Pacing pulse energies for pre-exciting infarct regions may be adjusted by programming the device via the telemetry interface in accordance with electrophysiological testing to determine an appropriate pacing pulse energy or may be adjusted automatically with an autocapture function such as described in U.S. Pat. No. 6,615,089, assigned to Cardiac Pacemakers, Inc. and hereby incorporated by reference.

An autocapture function is especially useful for the delivery of pre-excitation pacing to an infarct region because the excitability characteristics of the infarct region may change over time. For example, myocardial tissue damage may continue in a post-MI patient due to persistent cardiac ischemia. This may render the infarct region less excitable so as to require a greater pulse energy to achieve capture. The infarct region could also expand so that pacing pulses delivered to the selected site are no longer capable of achieving capture at any allowable pulse energy. Conversely, the infarct region could heal to such an extent that the region becomes more excitable and requires a lesser pacing pulse energy to achieve capture. The infarct region could also shrink due to the healing process so that the pre-excitation pacing is no longer being delivered to the optimum site for reducing remodeling. As described below, the device may be configured to deal with these situations by means of an autocapture function that continually or periodically adjusts pre-excitation pacing pulse energies and/or pre-excitation pacing sites in order maintain capture by the pre-excitation pacing pulses. The device controller may be programmed to perform algorithms for determining the appropriate pacing pulse energy and/or optimum pacing site(s) at periodic intervals or upon detection of a loss of capture by the pre-excitation pacing channel during normal device operation. The device could also perform the algorithms upon receipt of appropriate commands via the telemetry link from an external programmer.

In order to determine whether or not a pacing pulse has achieved capture, a capture verification test is performed in which an evoked response to the pre-excitation pacing pulse is detected. In an exemplary embodiment, verification of capture by pre-excitation pacing pulses is performed using the evoked response sensing channel 101 as shown in FIG. 2. The evoked response sensing channel includes a sense amplifier for sensing an evoked response generated after a pacing pulse is delivered. Alternatively, any of the device's sensing channels could be used to detect evoked responses. The evoked response sensing channel (or other sensing channel) is connected to a selected electrode of the pacemaker's sensing/pacing channels by means of the switch matrix 70. The electrode used to detect evoked responses may be the same electrode used to deliver the pacing pulse or another electrode disposed near the pacing site. After switching the input of the evoked response sensing channel to the selected electrode, a pacing pulse is output and an evoked response is detected, signifying the presence or loss of capture. Verifying capture by the pacing pulse involves comparing the evoked response electrogram signal following the pace to a predetermined threshold, which may be performed by the controller or other dedicated circuitry. If the evoked response electrogram signal exceeds the threshold, capture is presumed to have occurred. The sense amplifier of the evoked response sensing channel would normally be blanked during the capture verification test for a specified blanking period following a pacing pulse output by the pacing channel. The blanking period is then followed by a capture detection window during which an evoked response may be sensed by the evoked response sensing channel.

Figure 3:
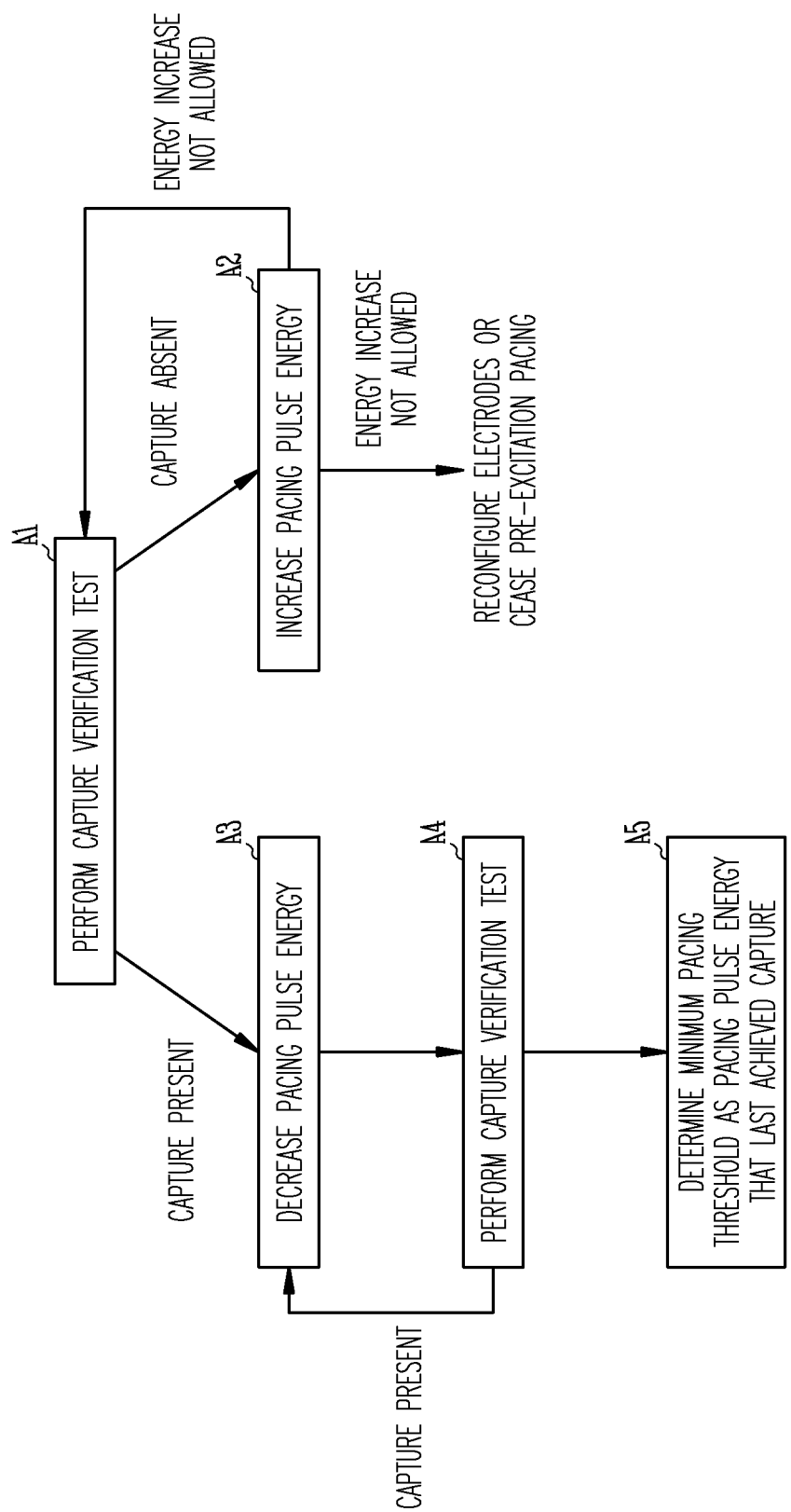
FIG. 3 illustrates an algorithm for adjustment of pacing pulse energy.

One aspect of an autocapture function involves the adjustment of pacing pulse energy in accordance with a determined minimum pacing threshold, referred to herein as an autothreshold procedure. FIG. 3 illustrates an example algorithm that could be executed by the device controller in order to automatically adjust the pre-excitation pulse energy for any selected pacing channel. In this algorithm, a minimum pacing threshold is determined, and the pacing pulse energy is then adjusted accordingly to match the determined minimum pacing threshold with an appropriate safety margin. The pacing pulse energy may be adjusted by changing the pulse voltage amplitude and/or the pulse width. At step A1, a capture verification test is performed on the pre-excitation pacing channel as described above. If capture is found to be absent, the pacing pulse energy is increased by a specified amount at step A2, and step A1 is repeated. If the increase of pacing pulse energy at step A2 is above that allowed by the device, an error is declared and pre-excitation pacing is ceased and/or the algorithm proceeds to the electrode reconfiguration algorithm described below. If capture is present after the test at step A1, the pacing pulse energy is decreased at step A3. Another capture verification test is then performed at step A4. If capture is present after the test at step A4, step A3 is repeated. When the test at step A4 indicates that the decrease in pacing pulse energy results in an absence of capture, the pacing threshold is then determined at step A5 as being the pacing pulse energy that last achieved capture (i.e., the pacing pulse energy before the immediately preceding decrease at step A3). The capture verification tests at steps A1 and A4 may be performed as pre-excitation paces are delivered during normal operation of the device.

Figure 4:
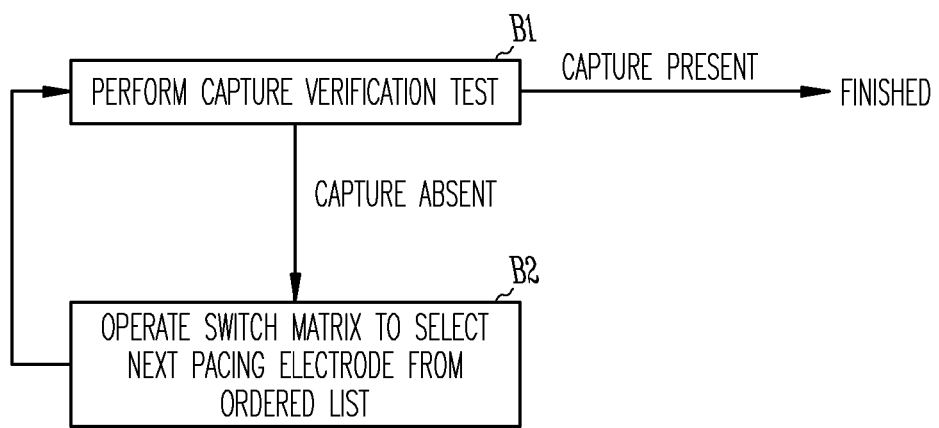
FIG. 4 illustrates an algorithm for reconfiguration of pacing electrodes.

The autocapture function may also include automatic reconfiguration of pacing electrodes that changes the pacing site(s) used for pre-excitation. Automatic pacing electrode reconfiguration may be performed upon detection of a loss of capture and when the autocapture function is unable to adjust the pacing pulse energy to a level adequate to regain capture using the available pacing pulse amplitudes and widths supported by the device. The pacing electrodes may also be reconfigured in order to change the pacing site(s) to an optimum location for reducing remodeling. Such an optimum location could be, for example, an excitable site as close as possible to the infarct itself. FIG. 4 illustrates an example algorithm for reconfiguration of pacing electrodes that may be performed for any selected pacing channel. The algorithm uses a preprogrammed ordered list of the available pacing electrodes that lists the electrodes in a preferred order of use. The ordered list may be determined by clinical testing in order to ensure that the reconfiguration algorithm selects the most optimum pacing location. The ordered list of available electrodes may also be continuously updated to reflect which of the available pacing electrodes are already in use and which electrodes have been found to be unable to achieve capture. At step B1, a capture verification test is performed for the presently selected electrode. Optionally, an autothreshold procedure as described above with reference to FIG. 3 may be performed to determine if capture is possible with the electrode by adjusting the pacing pulse energy. If no capture is achieved at step B1, the index is updated to reflect that the presently selected electrode has been unable to achieve capture and should not be used. The switch matrix is then operated at step B2 to select the next available pacing electrode from the ordered list for use, and the algorithm returns to step B1. When capture is achieved at step B1, the algorithm is finished. The pacing electrode reconfiguration algorithm can be performed whenever the autothreshold procedure reveals that a presently selected electrode is unable to achieve capture and may also be performed periodically or upon command in order to select an optimum pacing location. In the latter case, the pacing electrode index may be reset to restore available status to all electrodes to allow for the possibility that previously unexcitable pacing sites may have recovered their excitability due to tissue healing.

The autocapture and/or autothreshold functions as described herein may be incorporated in devices configured to deliver pacing therapy for the purpose of reversing or preventing cardiac remodeling in patients other than post-MI patients (e.g., patients with heart failure due to a number of causes). Other functionalities may also be provided for reversing or preventing remodeling. In particular, the autocapture and/or autothreshold functions as described herein may be incorporated in any of the devices described in U.S. Pat. Nos. 6,628,988, 6,973,349, 6,915,160, and 6,965,797.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for minimizing post-infarct ventricular remodeling, comprising:
   identifying an infarct region in a ventricle;
   delivering pacing pulses to one or more sites in proximity to the infarct region;
   wherein the pacing pulses are delivered in a manner that pre-excites the site or sites in proximity to the infarct region relative to other areas of the ventricle;
   verifying whether or not the pacing pulses delivered to the one or more sites have achieved capture;
   adjusting the energy of the pacing pulses if capture is not being achieved; and, changing the pacing site if capture is not being achieved and if the pacing pulse energy cannot be increased sufficiently to achieve capture, wherein the pacing site is changed in accordance with an ordered list of available electrodes that lists the electrodes in an order of preferred use reflecting their proximity to the infarct region.

2. The method of claim 1 wherein the energy of the pacing pulses is adjusted by changing the pulse amplitude.

3. The method of claim 1 wherein the energy of the pacing pulses is adjusted by changing the pulse width.

4. The method of claim 1 wherein the energy of the pacing pulses is adjusted by determining a minimum pacing threshold and setting the pacing pulse energy in accordance therewith.

5. The method of claim 1 further comprising updating the ordered list of available electrodes to reflect which of the available pacing electrodes are already in use and which electrodes have been found to be unable to achieve capture.

6. The method of claim 5 further comprising performing a capture verification test on a pacing electrode selected from the ordered list.

7. The method of claim 6 further comprising determining a minimum pacing threshold for a pacing electrode selected from the ordered list and setting the pacing pulse energy in accordance therewith.

8. The method of claim 1 further comprising periodically determining a minimum pacing threshold and setting the pacing pulse energy in accordance therewith.

9. The method of claim 1 further comprising periodically changing the pacing site in accordance with an ordered list that lists available pacing electrodes in an order of preferred use.

\* \* \* \* \*